(12) United States Patent
Törmäkangas et al.

(10) Patent No.: US 10,376,494 B2
(45) Date of Patent: *Aug. 13, 2019

(54) CARBOXAMIDE DERIVATIVE AND ITS DIASTEREOMERS IN STABLE CRYSTALLINE FORM

(71) Applicant: Orion Corporation, Espoo (FI)

(72) Inventors: Olli Törmäkangas, Turku (FI); Terhi Heikkinen, Lieto (FI)

(73) Assignee: Orion Corporation, Espoo (FI)

( * ) Notice: Subject to any disclaimer, the term of this patent is extended or adjusted under 35 U.S.C. 154(b) by 0 days.

This patent is subject to a terminal disclaimer.

(21) Appl. No.: 15/997,040

(22) Filed: Jun. 4, 2018

(65) Prior Publication Data

US 2018/0280355 A1    Oct. 4, 2018

Related U.S. Application Data

(63) Continuation of application No. 15/547,193, filed as application No. PCT/FI2016/050054 on Jan. 28, 2016, now Pat. No. 10,010,530.

(30) Foreign Application Priority Data

Jan. 30, 2015  (FI) .................. 20150033

(51) Int. Cl.

| A61K 31/4155 | (2006.01) |
| A61K 31/277 | (2006.01) |
| A61K 31/166 | (2006.01) |
| A61K 31/03 | (2006.01) |
| C07D 231/14 | (2006.01) |

(52) U.S. Cl.
CPC .......... *A61K 31/4155* (2013.01); *A61K 31/03* (2013.01); *A61K 31/166* (2013.01); *A61K 31/277* (2013.01); *C07D 231/14* (2013.01)

(58) Field of Classification Search
None
See application file for complete search history.

(56) References Cited

FOREIGN PATENT DOCUMENTS

| WO | WO 2011/051540 A1 | 5/2011 |
| WO | WO 2012/143599 A1 | 10/2012 |

OTHER PUBLICATIONS

International Search Report for PCT/FI2016/050054, issued by the European Patent Office, dated Mar. 24, 2016, 3 pages.
Caira: "Crystalline Polymorphism of Organic Compounds," *Topics in Current Chemistry*, Springer, Berlin, DE, vol. 198 (1998), pp. 163-208.
Naveen Chhabra et al.: "A review of drug isomerism and its significance," *International Journal of Applied and Basic Medical Research*, vol. 3, No. 1 (2013), p. 16.

*Primary Examiner* — Kamal A Saeed
(74) *Attorney, Agent, or Firm* — Finnegan, Henderson, Farabow, Garrett & Dunner, L.L.P.

(57) ABSTRACT

The present disclosure relates to solid crystalline forms of N—((S)-1-(3-(3-chloro-4-cyanophenyl)-1H-pyrazol-1-yl)-propan-2-yl)-5-(1-hydroxyethyl)-1H-pyrazole-3-carboxamide (I) and the diastereomers thereof, and to methods for preparing such crystalline forms. Compound (I) and the diastereomers thereof are potent androgen receptor (AR) modulators useful as a medicament.

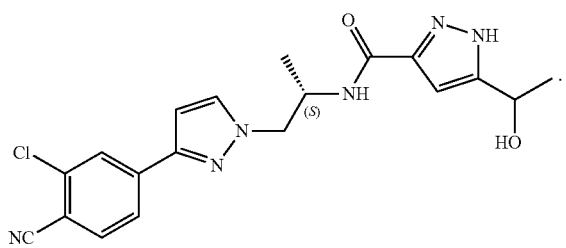

11 Claims, 3 Drawing Sheets

CARBOXAMIDE DERIVATIVE AND ITS DIASTEREOMERS IN STABLE CRYSTALLINE FORM

This is a continuation of pending application Ser. No. 15/547,193, filed Jul. 28, 2017, which is a national stage filing under 35 U.S.C. § 371 of International Application No. PCT/FI2016/050054, filed Jan. 28, 2016, which claims the benefit of priority of Finnish Patent Application No. 20150033, filed Jan. 30, 2015, all of which are incorporated herein by reference.

FIELD OF THE INVENTION

The present disclosure relates to solid crystalline forms of the pharmaceutical compound N—((S)-1-(3-(3-chloro-4-cyanophenyl)-1H-pyrazol-1-yl)-propan-2-yl)-5-(1-hydroxyethyl)-1H-pyrazole-3-carboxamide (I) and the diastereomers thereof, and to methods for preparing such crystalline forms.

BACKGROUND OF THE INVENTION

The compound N—((S)-1-(3-(3-chloro-4-cyanophenyl)-1H-pyrazol-1-yl)-propan-2-yl)-5-(1-hydroxyethyl)-1H-pyrazole-3-carboxamide (I) and manufacture thereof have been disclosed in WO 2011/051540. Compound (I) is a potent androgen receptor (AR) modulator useful in the treatment of cancer, particularly AR dependent cancer such as prostate cancer, and other diseases where AR antagonism is desired. Compound (I) is represented by the structure:

(I)

As the hydrogen atom of the pyrazole ring may exist in tautomeric equilibrium between the 1- and 2-position, it is recognized by the skilled person that the above structure and the chemical name "N—((S)-1-(3-(3-chloro-4-cyanophenyl)-1H-pyrazol-1-yl)-propan-2-yl)-5-(1-hydroxyethyl)-1H-pyrazole-3-carboxamide (I)," as referred to herein, is inclusive of the tautomer of compound (I), namely N—((S)-1-(3-(3-chloro-4-cyanophenyl)-1H-pyrazol-1-yl)-propan-2-yl)-3-(1-hydroxyethyl)-1H-pyrazole-5-carboxamide.

In addition to the chiral carbon atom shown in the chemical structure above, compound (I) has another chiral carbon atom with hydroxy group attached therein.

Therefore, compound (I) has two diastereomers, namely N—((S)-1-(3-(3-chloro-4-cyanophenyl)-1H-pyrazol-1-yl)propan-2-yl)-5-((S)-1-hydroxyethyl)-1H-pyrazole-3-carboxamide (Ia)

and N—((S)-1-(3-(3-chloro-4-cyanophenyl)-1H-pyrazol-1-yl)propan-2-yl)-5-((R)-1-hydroxyethyl)-1H-pyrazole-3-carboxamide (Ib).

Due to the tautomeric equilibrium of the hydrogen atom between the 1- and 2-position in the pyrazole ring, the chemical name of diastereomers (Ia) and (Ib) are inclusive of the tautomers of (Ia) and (Ib), similarly to compound (I) as explained above.

Compounds (Ia) and (Ib) are also potent androgen receptor (AR) modulators useful in the treatment of cancer, particularly AR dependent cancer such as prostate cancer, and other diseases where AR antagonism is desired.

SUMMARY OF THE INVENTION

It has now been found that compound (I) and its diastereomers (Ia) and (Ib) can be obtained in a stable and substantially pure crystalline form by crystallization under certain conditions.

Thus, the present disclosure provides, as one aspect, N—((S)-1-(3-(3-chloro-4-cyanophenyl)-1H-pyrazol-1-yl)-propan-2-yl)-5-(1-hydroxyethyl)-1H-pyrazole-3-carboxamide (I) in crystalline form I.

In another aspect, the present disclosure provides diastereomer N—((S)-1-(3-(3-chloro-4-cyanophenyl)-1H-pyrazol-1-yl)propan-2-yl)-5-((S)-1-hydroxyethyl)-1H-pyrazole-3-carboxamide (Ia) in crystalline form I'.

In yet another aspect, the present disclosure provides diastereomer N—((S)-1-(3-(3-chloro-4-cyanophenyl)-1H-pyrazol-1-yl)propan-2-yl)-5-((R)-1-hydroxyethyl)-1H-pyrazole-3-carboxamide (Ib) in crystalline form I".

In yet another aspect, the present disclosure provides N—((S)-1-(3-(3-chloro-4-cyanophenyl)-1H-pyrazol-1-yl)-propan-2-yl)-5-(1-hydroxyethyl)-1H-pyrazole-3-carboxamide (I) in crystalline form I as defined herein, substantially free of any other crystalline form of compound (I).

In yet another aspect, the present disclosure provides diastereomer N—((S)-1-(3-(3-chloro-4-cyanophenyl)-1H-pyrazol-1-yl)propan-2-yl)-5-((S)-1-hydroxyethyl)-1H-pyrazole-3-carboxamide (Ia) in crystalline form I' as defined herein, substantially free of any other crystalline form of compound (Ia).

In yet another aspect, the present disclosure provides diastereomer N—((S)-1-(3-(3-chloro-4-cyanophenyl)-1H-pyrazol-1-yl)propan-2-yl)-5-((R)-1-hydroxyethyl)-1H-pyrazole-3-carboxamide (Ib) in crystalline form I" as defined herein, substantially free of any other crystalline form of compound (Ib).

The crystalline forms I, I' and I" are stable during pharmaceutical processing and storage, and are therefore particularly suitable in the preparation of pharmaceutical formulations.

DETAILED DESCRIPTION OF THE INVENTION

Crystalline form I of compound (I), crystalline form I' of compound (Ia) and crystalline form I" of compound (Ib) have been characterized by X-ray powder diffraction (XRPD) studies.

Accordingly, in one aspect, the present disclosure provides crystalline form I of N—((S)-1-(3-(3-chloro-4-cyanophenyl)-1H-pyrazol-1-yl)-propan-2-yl)-5-(1-hydroxyethyl)-1H-pyrazole-3-carboxamide (I) having an X-ray powder diffraction pattern comprising characteristic peaks at about 8.5, 10.4, 16.6, 16.9, and 24.3 degrees 2-theta.

In another aspect, the present disclosure provides crystalline form I' of N—((S)-1-(3-(3-chloro-4-cyanophenyl)-1H-pyrazol-1-yl)propan-2-yl)-5-((S)-1-hydroxyethyl)-1H-pyrazole-3-carboxamide (Ia) having an X-ray powder diffraction pattern comprising characteristic peaks at about 9.3, 15.7, 17.0, 24.1 and 25.1 degrees 2-theta.

In yet another aspect, the present disclosure provides crystalline form I" of N—((S)-1-(3-(3-chloro-4-cyanophenyl)-1H-pyrazol-1-yl)propan-2-yl)-5-((R)-1-hydroxyethyl)-1H-pyrazole-3-carboxamide (Ib) having an X-ray powder diffraction pattern comprising characteristic peaks at about 9.2, 10.9, 15.1, 15.8 and 22.1 degrees 2-theta.

In yet another aspect, the present disclosure provides crystalline form I of N—((S)-1-(3-(3-chloro-4-cyanophenyl)-1H-pyrazol-1-yl)-propan-2-yl)-5-(1-hydroxyethyl)-1H-pyrazole-3-carboxamide (1) having an X-ray powder diffraction pattern comprising characteristic peaks at about 6.4, 8.5, 9.6, 9.7, 10.4, 12.8, 13.6, 14.9, 15.9, 16.6, 16.9, 18.7, 19.2, 21.8, 24.3, and 25.5 degrees 2-theta.

In yet another aspect, the present disclosure provides crystalline form I' of N—((S)-1-(3-(3-chloro-4-cyanophenyl)-1H-pyrazol-1-yl)propan-2-yl)-5-((S)-1-hydroxyethyl)-1H-pyrazole-3-carboxamide (Ia) having an X-ray powder diffraction pattern comprising characteristic peaks at about 9.3, 11.4, 11.5, 13.6, 14.7, 14.9, 15.7, 16.1, 17.0, 17.7, 18.5, 19.1, 20.5, 21.5, 22.1, 22.6, 23.2, 23.6, 24.1, 25.1, 26.2 and 27.2 degrees 2-theta.

In yet another aspect, the present disclosure provides crystalline form I" of N—((S)-1-(3-(3-chloro-4-cyanophenyl)-1H-pyrazol-1-yl)propan-2-yl)-5-((R)-1-hydroxyethyl)-1H-pyrazole-3-carboxamide (Ib) having an X-ray powder diffraction pattern comprising characteristic peaks at about 7.9, 9.2, 10.9, 13.2, 14.8, 15.1, 15.5, 1.5.8, 16.9, 18.4, 20.2, 20.5, 21.8, 22.1 and 24.3 degrees 2-theta.

Figure 1:
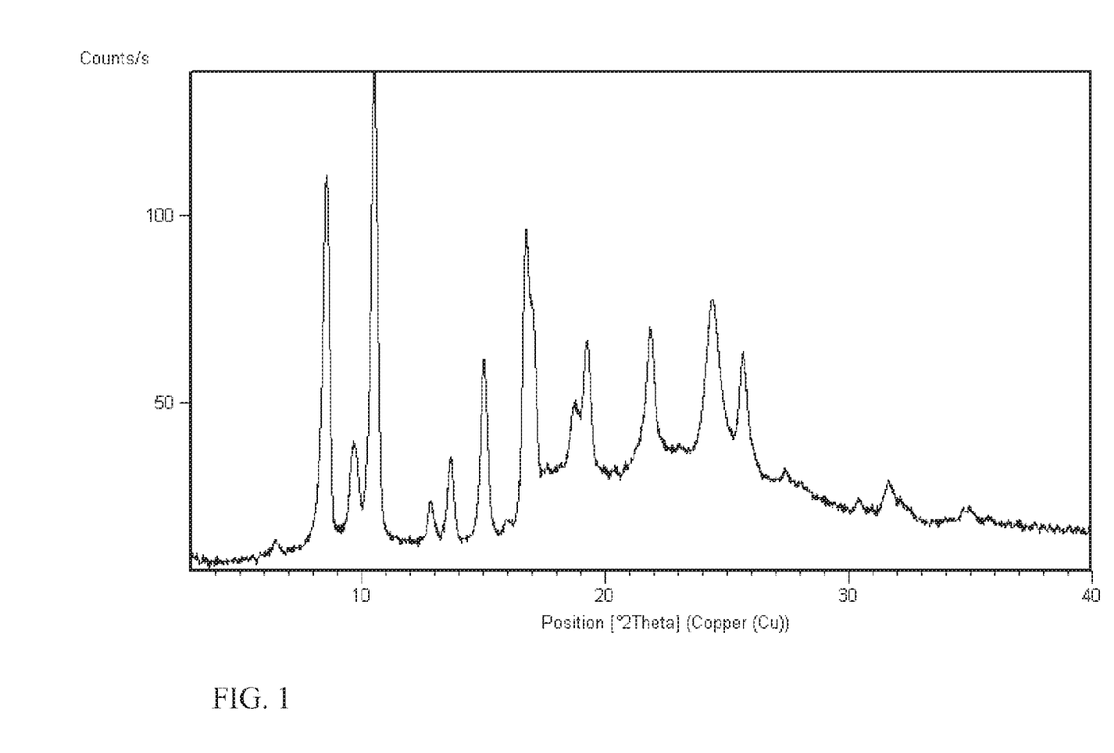
FIG. 1 shows the X-ray powder diffraction pattern of the crystalline form I of compound (I) obtained in Example 1.

In still another aspect, the present disclosure provides crystalline form I of N—((S)-1-(3-(3-chloro-4-cyanophenyl)-1H-pyrazol-1-yl)-propan-2-yl)-5-(1-hydroxyethyl)-1H-pyrazole-3-carboxamide (I) characterized in that it provides an X-ray powder diffraction pattern substantially as illustrated in FIG. 1.

Figure 2:
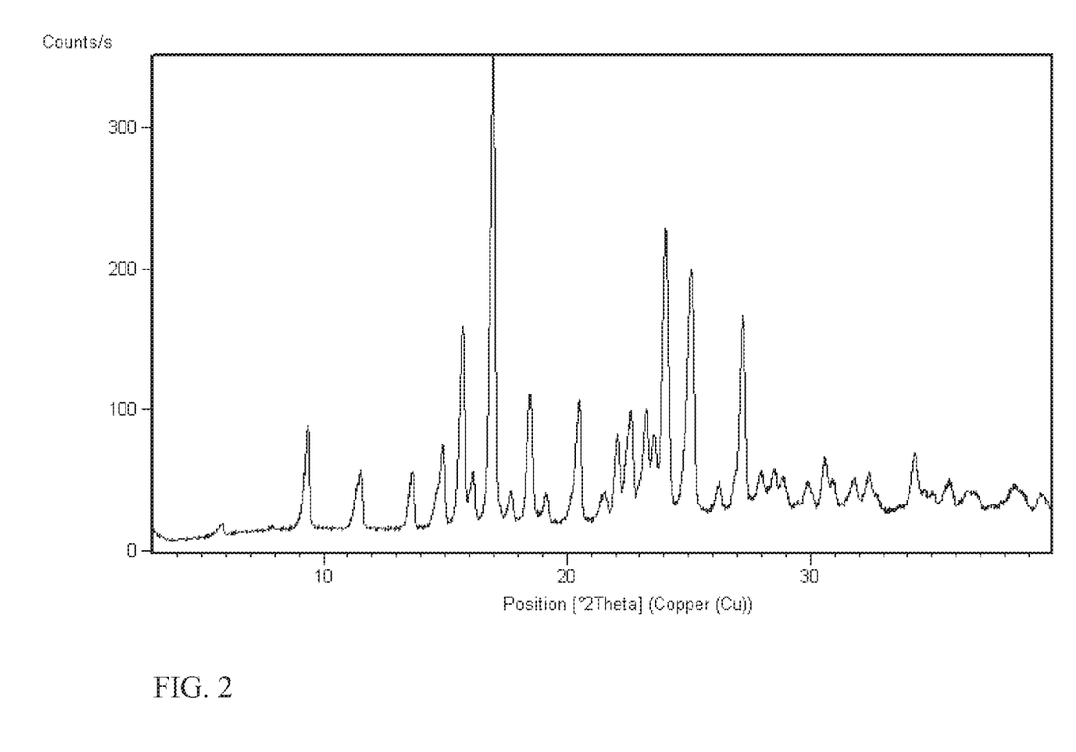
FIG. 2 shows the X-ray powder diffraction pattern of the crystalline form of compound (Ia) obtained in Example 4.

According to still another aspect, the present disclosure provides crystalline form I' of N—((S)-1-(3-(3-chloro-4-cyanophenyl)-1H-pyrazol-1-yl)propan-2-yl)-5-((S)-1-hydroxyethyl)-1H-pyrazole-3-carboxamide (Ia) characterized in that it provides an X-ray powder diffraction pattern substantially as illustrated in FIG. 2.

Figure 3:
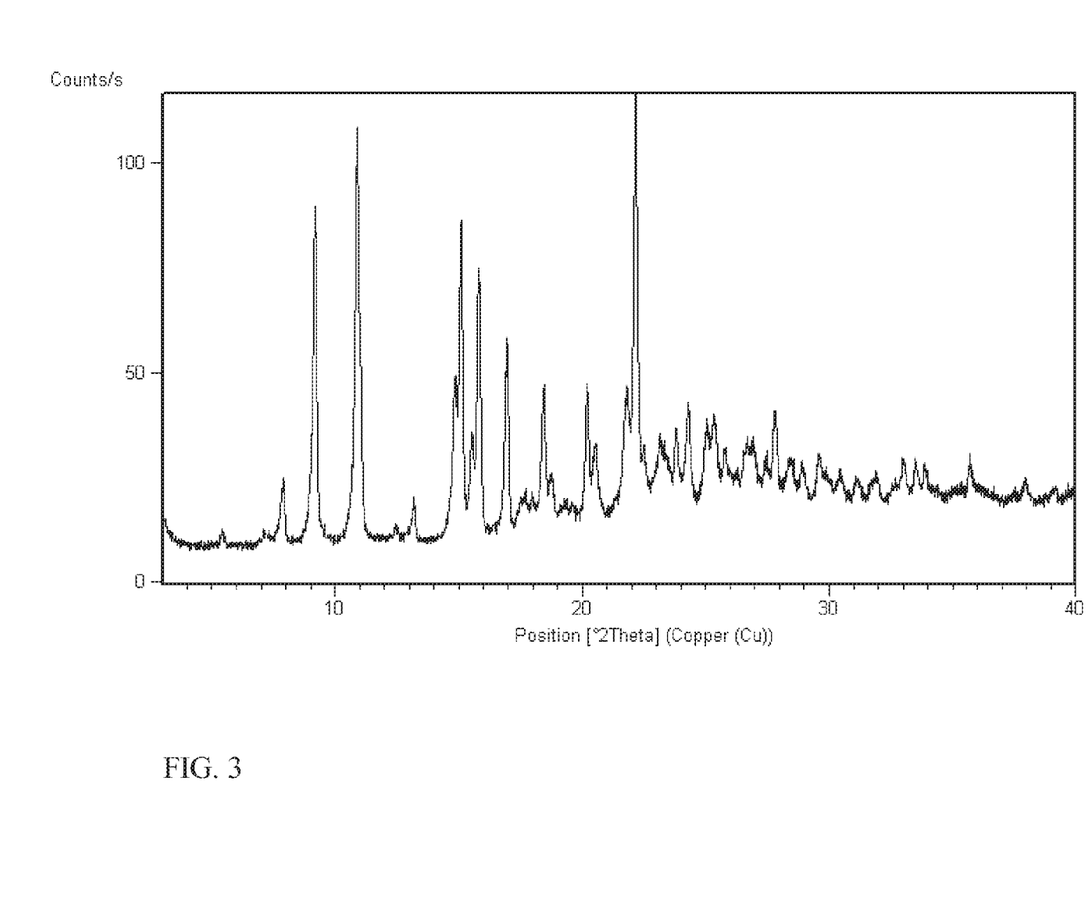
FIG. 3 shows the X-ray powder diffraction pattern of the crystalline form of compound (Ib) obtained in Example 7.

According to still another aspect, the present disclosure provides crystalline form I" of N—((S)-1-(3-(3-chloro-4-cyanophenyl)-1H-pyrazol-1-yl)propan-2-yl)-5-((R)-1-hydroxyethyl)-1H-pyrazole-3-carboxamide (Ib) characterized in that it provides an X-ray powder diffraction pattern substantially as illustrated in FIG. 3.

It is recognized by the skilled person that the X-ray powder diffraction pattern peak positions referred to herein can be subject to variations of +/− 0.15 degrees 2-theta according to various factors such as temperature, concentration, and instrumentation used. Therefore, signals and peak positions are referred to herein as being at "about" specific values.

According to still another aspect, the present disclosure provides a process for preparing crystalline form I, or I" of N—((S)-1-(3-(3-chloro-4-cyanophenyl)-1H-pyrazol-1-yl)propan-2-yl)-5-(1-hydroxyethyl)-1H-pyrazole-3-carboxamide (I), N—((S)-1-(3-(3-chloro-4-cyanophenyl)-1H-pyrazol-1-yl)propan-2-yl)-5-((S)-1-hydroxyethyl)-1H-pyrazole-3-carboxamide (Ia) N—((S)-1-(3-(3-chloro-4-cyanophenyl)-1H-pyrazol-1-yl)propan-2-yl)-5-((R)-1-hydroxyethyl)-1H-pyrazole-3-carboxamide (Ib), respectively, comprising a) mixing N—((S)-1-(3-(3-chloro-4-cyanophenyl)-1H-pyrazol-1-yl) propan-2-yl)-5-(1-hydroxyethyl)-1H-pyrazole-3-carboxamide (I), N—((S)-1-(3-(3-chloro-4-cyanophenyl)-1H-pyrazol-1-yl)propan-2-yl)-5-((S)-1-hydroxyethyl)-1H-pyrazole-3-carboxamide (Ia) or N—((S)—((S)-1-(3-(3-chloro-4-cyanophenyl)-1H-pyrazol-1-yl)propan-2-yl)-5-((R)-1-hydroxyethyl)-1H-pyrazole-3-carboxamide (Ib) with a mixture of acetonitrile and water;

b) heating the mixture from step a) to form a solution, c) cooling the solution from step b) to about 0-50° C.; and d) isolating the crystalline form.

In still another aspect, the present disclosure provides a process for the manufacture of diastereomer (Ia) or (Ib) comprising a) reducing compound of formula (1)

(1)

wherein R is H or $C_{1-6}$ alkyl, with a ketoreductase enzyme to obtain compound of formula (2) in optically active form, wherein R is as defined above;

b) optionally protecting the hydroxyl group of compound of formula (2), c) in case R is an $C_{1-6}$ alkyl, subjecting the compound of formula (2), wherein the hydroxyl group is optionally protected, to cleavage of the ester bond to obtain compound (3);

wherein the hydroxyl group is optionally protected; and d) treating compound (3), wherein the hydroxyl group is optionally protected, with (S)-4-(1-(2-aminopropyl)-1H-pyrazol-3-yl)-2-chlorobenzonitrile, and, in case the hydroxyl group is protected, deprotecting the hydroxyl group, to obtain compound (Ia) or (Ib).

Compound (I) can be synthetized using the procedures described in WO 2011/051540.

Pure diastereomers (Ia) and (Ib) can be suitably synthetized, for example, using ketoreductase enzymes (KREDs) for both S- and R-selective reduction of compound 1 to compound 2 as shown in Scheme 1, wherein R is H or $C_{1-6}$alkyl.

For example, Codexis KRED-130 and KRED-NADH-110 enzymes are useful for obtaining excellent stereoselectivity, even stereospecificity. In Scheme 1 the starting material t is preferably an ester (R=$C_{1-6}$ alkyl), for example ethyl ester (R=ethyl), such as to facilitate extraction of the product into the organic phase as the compound where R=H has a tendency to remain in the water phase. Intermediate 2 can be protected, preferably with silyl derivatives such as tert-butyldiphenylsilyl, in order to avoid esterification in amidation step. In the case of R=$C_{1-6}$ alkyl, ester hydrolysis is typically performed before amidation step, preferably in the presence of LiOH, NaOH or KOH. Amidation from compound 3 to compound 5 is suitably carried out using EDCI HBTU, DIPEA system but using other typical amidation methods is also possible. Deprotection of 5 give pure diastereomers (Ia) and (Ib).

Pyrazole ring without NH substitution is known tautomerizable functionality and is described here only as single tautomer but every intermediate and end product here can exist in both tautomeric forms at the same time.

The stereochemistry of the compounds can be confirmed by using optically pure starting materials with known absolute configuration as demonstrated in Scheme 2, wherein R=H or $C_{1-6}$ alkyl, preferably alkyl, for example ethyl. The end products of Scheme 2 are typically obtained as a mixture of tautomers at +300K $^1$H-NMR analyses in DMSO.

Scheme 2. Synthesis pathway to stereoisomers by using starting materials with known absolute configuration The crystalline forms I, I' and I" of compounds (I), (Ia) and (Ib), respectively, can be prepared, for example, by dissolving the compound in question in an acetonitrile:water mixture having volume ratio from about 85:15 to about 99:1, such as from about 90:10 to about 98:2, for example about 95:5, under heating and slowly cooling the solution until the crystalline form precipitates from the solution. The concentration of the compound in the acetonitrile:water solvent mixture is suitably about 1 kg of the compound in 5-25 liters of acetonitrile:water solvent mixture, for example 1 kg of the compound in 10-20 liters of acetonitrile:water solvent mixture. The compound is suitably dissolved in the acetonitrile:water solvent mixture by heating the solution, for example near to the reflux temperature, for example to about 60-80° C. for example to about 75° C., under stirring and filtering if necessary. The solution is suitably then cooled to about 0-50° C., for example to about 5-35° C., for example to about RT, over about 5 to about 24 hours, for example over about 6 to 12 hours, and stirred at this temperature for about 3 to 72 hours, for example for about 5 to 12 hours. The obtained crystalline product can then be filtered, washed, and dried. The drying is suitably carried out in vacuum at about 40 to 60° C., for example at 55° C., for about 1 to 24 hours, such as for about 2 to 12 hours, for example 2 to 6 hours.

The crystalline forms I, I' and I" of compounds (I), (Ia) and (Ib), respectively, are useful as medicaments and can be formulated into pharmaceutical dosage forms, such as tablets and capsules for oral administration, by mixing with pharmaceutical excipients known in the art.

The disclosure is further illustrated by the following examples.

Example 1. Crystallization of N—((S)-1-(3-(3-chloro-4-cyanophenyl)-1H-pyrazol-1-yl)-propan-2-yl)-5-hydroxyethyl)-1H-pyrazole-3-carboxamide (I)

N—((S)-1-(3-(3-chloro-4-cyanophenyl)-1H-pyrazol-1-yl)-propan-2-yl)-5-(1-hydroxy-ethyl)-1H-pyrazole-3-carboxamide (I) (5 g), 71.25 ml of acetonitrile, and 3.75 ml of distilled water were charged to a flask, and the mixture was heated up to 75° C. The mixture was slowly cooled down to RT and stirred at RT for 3 days. The solid obtained was filtered and washed twice with acetonitrile:water (9.5 ml 0.5 ml). The product was dried under vacuum at 40° C. and finally at 60° C. to obtain 4.42 g of crystalline title compound (yield of 88%) which was used in X-ray diffraction study.

Example 2. X-Ray Diffraction Study of Crystalline Compound (I)

The crystalline form of compound (I) obtained in Example 1 was analysed by X-ray powder diffraction method. The measurements were performed with the X-ray powder diffractometer PANalytical X'Pert PRO at room temperature using Cu filled X-ray tube (45 kV×40 mA) as the X-ray source, a fixed 1° anti-scatter slit, a programmable divergence slit with 5.0 mm irradiated length and the real time multiple strip detector X'Celerator. Data collection was done in 0.008° steps at a scan speed of 1°/min in the range of 3-80° 2θ. The crystalline form was characterized by an X-ray powder diffraction pattern as shown in FIG. 1 and exhibiting characteristic peaks at about the following 2-theta values:

| Angle 2-theta ° |
| --- |
| 6.4 |
| 8.5 |
| 9.6 |
| 9.7 |
| 10.4 |
| 12.8 |
| 13.6 |
| 14.9 |
| 15.9 |
| 16.6 |
| 16.9 |
| 18.7 |
| 19.2 |
| 21.8 |
| 24.3 |
| 25.5 |

Example 3. Synthesis of N—((S)-1-(3-(3-chloro-4-cyanophenyl)-1H-pyrazol-1-yl)-propan-2-yl)-5-((S)-1-hydroxyethyl)-1H-pyrazole-3-carboxamide (Ia)

a) Ethyl-5-((S)-1-hydroxyethyl)-1H-pyrazole-3-carboxylate

MgSO₄×7H₂O (341 mg), NADP monosodium salt (596 mg), D(+)-glucose (9.26 g) and optimized enzyme CDX-901 lyophilized powder (142 mg) were added to 0.2 mM of KH₂PO₄ buffer (pH 7.0, 709 ml) to prepare solution I. To this solution I was added solution II which contained ethyl-5-acetyl-1H-pyrazole-3-carboxylate (8.509 g; 46.70 mmol), EtOH (28 ml) and KRED-130 (NADPH ketoreductase, 474 mg). The mixture was agitated at 30-32° C. for 5.5 h (monitoring by HPLC) and allowed to cool to RT. The mixture was evaporated to smaller volume and the residue was agitated with diatomaceous earth and filtered. The mother liquid was extracted with 3×210 ml of EtOAc and dried. The solution was filtered through silica (83 g) and evaporated to dryness to give 7.40 g of the title compound. The optical purity was 100% ee.

b) Ethyl 5-((S)-1-((tert-butyldiphenylsilyl)oxy)-ethyl)-1H-pyrazole-3-carboxylate

Diphenyl-tert-butyl chlorosilane (7.48 g, 27.21 mmol) was added in 26 ml of DMF to a mixture of compound of Example 3(a) (5.00 g, 27.15 mmol) and imidazole (2.81 g, 41.27 mmol) in DMF (50 ml) at RT. The mixture was stirred at RT for 24 h. Saturated aqueous NaHCO₃ (56 ml) and water (56 ml) were added and the mixture was stirred at RT for 20 min. The mixture was extracted with 2×100 ml of EtOAc. Combined organic phases were washed with water (1×100 ml, 1×50 ml), dried (Na₂SO₄), filtered and concentrated to give 10.92 g of crude title compound.

c) 5-((S)-1-((tert-Butyldiphenylsilyl)oxy)ethyl)-1H-pyrazole-3-carboxylic acid

2 M NaOH (aq) (38.8 ml; 77.5 mmol) was added to a solution of the compound of Example 3(b) (10.9 g, 25.8 mmol) in 66 ml of THF. The mixture was heated up to reflux temperature. Heating was continued for 2.5 h and THF was removed in vacuum. Water (40 ml) and EtOAc (110 ml) were added. Clear solution was obtained after addition of more water (10 ml). Layers were separated and aqueous phase was extracted with 100 ml of EtOAc. Combined organic phases were dried (Na₂SO₄), filtered and concentrated to give 9.8 g of the title compound.

d) 5-((S)-1-((tert-Butyldiphenylsilyl)oxy)ethyl)-N—((S)-1-(3-(3-chloro-4-cyanophenyl)-1H-pyrazol-1-yl)propan-2-yl)-1H-pyrazole-3-carboxamide Under nitrogen atmosphere HBTU (0.84 g; 2.22 mmol), EDCI×HCl (3.26 g; 17.02 mmol) and (S)-4-(1-(2-aminopropyl)-1H-pyrazol-3-yl)-2-chlorobenzonitrile (3.86 g; 14.80 mmol) were added to a mixture of crude compound of Example 3(c) (8.68 g; purity 77.4 area-%) and DIPEA (2.20 g; 17.02 mmol) in DCM (50 ml). The mixture was stirred at RT for 46 h (6 ml of DCM was added after 20 h). The mixture was washed with 3×20 ml of water, dried (Na₂SO₄), filtered and concentrated to give 13.7 g of crude title compound.

e) N—((S)-1-(3-(3-chloro-4-cyanophenyl)-1H-pyrazol-1-yl)propan-2-yl)-5-((S)-1-hydroxyethyl)-1H-pyrazole-3-carboxamide (Ia)

TBAF hydrate (Bu$_4$NF×3H$_2$O; 2.34 g; 7.40 mmol) in 10 ml of THF was added to the solution of the compound of Example 3(d) (9.43 g; 14.79 mmol) in THF (94 ml) at 0° C. under nitrogen atmosphere. Stirring was continued at RT for 21.5 h and the mixture was concentrated. DCM (94 ml) was added to the residue and the solution was washed with 3×50 ml of water, dried (Na$_2$SO$_4$), filtered and concentrated. Crude product was purified by flash chromatography (EtOAc/n-heptane) to give 2.1 g of the title compound. $^1$H-NMR (400 MHz; d6-DMSO; 300K): Major tautomer (~85%): δ 1.11 (d, 3H), 1.39 (d, 3H), 4.24-4.40 (m, 2H), 4.40-4.50 (m, 1H), 6.41 (s, 1H), 6.93 (d, 1H), 7.77-7.82 (m, 1H), 7.88-8.01 (m, 2H), 8.08 (s, 1H), 8.19 (d, 1H), 13.02 (broad s, 1H). Minor tautomer ~15%) δ 1.07-1.19 (m, 3H), 1.32-1.41 (m, 3H), 4.24-4.40 (m, 2H), 4.40-4.50 (m, 1H), 6.80 (broad s, 1H), 6.91-6.94 (m, 1H), 7.77-7.82 (m, 1H), 7.88-8.01 (m, 2H), 8.05-8.09 (m, 1H), 8.31 (d, 1H), 13.10 (broad s, 1H).

Example 4. Crystallization of N—((S)-1-(3-(3-chloro-4-cyanophenyl)-1H-pyrazol-1-yl)propan-2-yl)-5-((S)-1-hydroxyethyl)-1H-pyrazole-3-carboxamide (Ia)

N—((S)-1-(3-(3-chloro-4-cyanophenyl)-1H-pyrazol-1-yl)propan-2-yl)-5-((S)-1-hydroxyethyl)-1H-pyrazole-3-carboxamide (Ia) (5.00 g; 12.54 mmol) was mixed with 47.5 ml of ACN and 2.5 ml of water. The mixture was heated until compound (Ia) was fully dissolved. The solution was allowed to cool slowly to RT to form a precipitate. The mixture was then further cooled to 0° C. and kept in this temperature for 30 min. The mixture was filtered and the precipitate was dried under vacuum to obtain 4.50 g of crystalline title compound which was used in the X-ray diffraction study.

Example 5. X-Ray Diffraction Study of Crystalline Compound (Ia)

The crystalline form of compound (Ia) obtained in Example 4 was analysed by X-ray powder diffraction method as described in Example 2. The crystalline form was characterized by an X-ray powder diffraction pattern as shown in FIG. 2 and exhibiting characteristic peaks at about the following 2-theta values:

| Angle 2-theta ° |
| --- |
| 9.3 |
| 11.4 |
| 11.5 |
| 13.6 |
| 14.7 |
| 14.9 |
| 15.7 |
| 16.1 |
| 17.0 |
| 17.7 |
| 18.5 |
| 19.1 |
| 20.5 |
| 21.5 |
| 22.1 |
| 22.6 |
| 23.2 |
| 23.6 |
| 24.1 |
| 25.1 |
| 26.2 |
| 27.2 |

Example 6. Synthesis of N—((S)-1-(3-(3-chloro-4-cyanophenyl)-1H-pyrazol-1-yl)-propan-2-yl)-5-((R)-1-hydroxyethyl)-1H-pyrazole-3-carboxamide (Ib)

a) Ethyl-5-((R)-1-hydroxyethyl)-1H-pyrazole-3-carboxylate

Potassium dihydrogen phosphate buffer (Solution I) was prepared by dissolving potassium dihydrogen phosphate (11.350 g, 54.89 mmol) to water (333 ml) and adjusting pH of the solution to 7.0 by addition of 5 M solution of NaOH. MgSO$_4$×7 H$_2$O (1.650 g), NAD monosodium salt (0.500 g), D(+)-glucose (10.880 g) and optimised enzyme CDX-901 lyophilised powder (0.200 g) were added to Solution I. To this solution (Solution II) were added KRED-NADH-110 (0.467 g), ethyl-5-acetyl-1H-pyrazole-3-carboxylate (10.00 g; 54.89 mmol) and 2-methyltetrahydro-furan (16 ml). The mixture was agitated at 30° C. for 11 h and allowed to cool to RT overnight. The pH of the mixture was kept at 7 by addition of 5 M solution of NaOH. The mixture was evaporated to a smaller volume. The evaporation residue was agitated for 10 min with diatomaceous earth (40 g) and activated charcoal (0.54 g), and filtered. Material on the filter was washed with water (40 ml) and the washings were combined with the filtrate. Layers were separated and aqueous phase was extracted with EtOAc (450 ml and 2×270 ml). Combined organic phases were dried over Na$_2$SO$_4$, filtered and evaporated to dryness to give 9.85 g of the title compound (100% ee).

b) Ethyl-5-((R)-1-((tert-butyldiphenylsilyl)oxy)ethyl)-1H-pyrazole-3-carboxylate

Imidazole (5.32 g; 78.08 mmol) was added to a DCM (67 ml) solution of the compound of Example 6(a) (9.85 g; 53.48). The mixture was stirred until all reagent was dissolved and tert-butyldiphenyl chlorosilane (13.21 ml; 50.80 mmol) was added to the mixture. The mixture was stirred for 1.5 h, 70 ml of water was added and stirring was continued for 15 min. Layers were separated and organic phase was washed with 2×70 ml of water and dried over $Na_2SO_4$, filtered and concentrated to give 22.07 g of crude title compound.

c) 5-((R)-1-((tert-Butyldiphenylsilyl)oxy)ethyl)-1H-pyrazole-3-carboxylic acid

Compound of Example 6(b) (11.3 g; 26.74 mmol; theoretical yield from the previous step) was dissolved in 34 ml of THF and 50 ml of 2 M NaOH (aq.) was added. The mixture was heated under reflux temperature for 70 min. The mixture was extracted with 2×55 ml of EtOAc and combined organic phases were washed with brine, dried over $Na_2SO_4$, filtered and concentrated. Evaporation residue was triturated in 250 ml of n-heptane, filtered and dried to give 17.58 g of crude title compound.

d) 5-((R)-1-((tert-Butyldiphenylsilyl)oxy)ethyl)-N—((S)-1-(3-(3-chloro-4-cyanophenyl)-1H-pyrazol-1-yl)propan-2-yl)-1H-pyrazole-3-carboxamide A mixture of the compound of Example 6(c) (11.14 g; 26.75 mmol; theoretical yield from the previous step), 91 ml of DCM, HBTU (1.52 g; 4.01 mmol), EDCI×HCl (5.90 g; 30.76 mmol), (S)-4-(1-(2-aminopropyl)-1H-pyrazol-3-yl)-2-chlorobenzonitrile (6.97 g; 26.75 mmol) and DIPEA (3.98 g; 30.76 mmol) was stirred at RT for 3 h and at 30° C. for 22 h. The mixture was washed with 2×90 ml of 0.5 M HCl and 4×90 ml of water, dried over $Na_2SO_4$, filtered and concentrated. Crude product was purified by flash column chromatography (n-heptane-EtOAc) to give 16.97 g of title compound.

e) N—((S)-1-(3-(3-chloro-4-cyanophenyl)-1H-pyrazol-1-yl)propan-2-yl)-5-((R)-1-hydroxyethyl)-1H-pyrazole-3-carboxamide (Ib)

A mixture of the compound of Example 6(d) (6.09 g; 9.56 mmol), 61 ml of THF and TBAF was stirred at 40° C. for 6.5 h. The mixture was concentrated and 61 ml of EtOAc was added to the evaporation residue. Solution was washed with 2×50 ml of 0.5 M HCl and 4×50 ml of water, dried over $Na_2SO_4$, filtered and concentrated. Crude product was purified by flash column chromatography (n-heptane-EtOAc) to give 1.71 g of the title compound. $^1$H-NMR (400 MHz; d6-DMSO; 300K): Major tautomer (~85%): δ 1.10 (d, 3H), 1.38 (d, 3H), 4.14-4.57 (m, 2H), 5.42 (d, 1H), 6.39 (s, 1H), 6.86-6.98 (m, 1H), 7.74-7.84 (m, 1H), 7.86-8.02 (m, 2H), 8.08 (s, 1H), 8.21 (d, 1H), 13.04 (broad s, 1H), Minor tautomer (~15%) δ 0.95-1.24 (m, 3H), 1.25-1.50 (m, 3H), 4.14-4.57 (m, 2H), 4.60-4.90 (m, 1H), 5.08 (d, 1H), 6.78 (broad s, 1H), 6.86-6.98 (m, 1H), 7.77-7.84 (m, 1H), 7.86-8.02 (m, 2H), 8.02-8.12 (m, 1H), 8.32 (d, 1H), 13.11 (broad s, 1H).

Example 7. Crystallization of N—((S)-1-(3-(3-chloro-4-cyanophenyl)-1H-pyrazol-1-yl)propan-2-yl)-5-((R)-1-hydroxyethyl)-1H-pyrazole-3-carboxamide (Ib)

N—((S)-1-(3-(3-chloro-4-cyanophenyl)-1H-pyrazol-1-yl)propan-2-yl)-5-((R)-1-hydroxyethyl)-1H-pyrazole-3-carboxamide (Ib) (3.7 g; 9.28 mmol) was mixed with 70 ml of ACN and 3.5 ml of water. The mixture was heated to reflux temperature until compound (Ib) was fully dissolved. The solution was allowed to cool slowly. The mixture was filtered at 50° C. to obtain 6.3 mg of the precipitate. Mother liquid was cooled to 41° C. and filtered again to obtain 20.7 mg of the precipitate. Obtained mother liquid was then cooled to 36° C. and filtered to obtain 173 mg of the precipitate. The final mother liquid was cooled to RT, stirred overnight, cooled to 0° C., filtered, washed with cold ACN:water (1:1) and dried to obtain 2.71 g of the precipitate. The precipitates were checked for optical purity and the last precipitate of crystalline title compound (optical purity 100%) was used in the X-ray diffraction study.

Example 8. X-Ray Diffraction Study of Crystalline Compound (Ib)

The crystalline form of compound (Ib) obtained in Example 7 was analysed by X-ray powder diffraction method as described in Example 2. The crystalline form was characterized by an X-ray powder diffraction pattern as shown in FIG. 3 and exhibiting characteristic peaks at about the following 2-theta values:

| Angle 2-theta ° |
| --- |
| 7.9 |
| 9.2 |
| 10.9 |
| 13.2 |
| 14.8 |
| 15.1 |
| 15.5 |
| 15.8 |
| 16.9 |
| 18.4 |
| 20.2 |
| 20.5 |

| Angle 2-theta ° |
| --- |
| 21.8 |
| 22.1 |
| 24.3 |

Example 9. Synthesis of Ethyl-5-((S) 1-hydroxyethyl)-1H-pyrazole-3-carboxylate Zinc trifluoromethanesulfonate (0.259 g; 0.713 mmol) and (S)-(−)-3-butyn-2-ol (0.25 g; 3.57 mmol) were added to 0.75 ml (5.35 mmol) of $Et_3N$ under nitrogen atmosphere. Ethyldiazoacetate (0.45 ml; 4.28 mmol) was added slowly and the mixture was heated at 100° C. for 2 h. The mixture was cooled to RT and 5 ml of water was added. The mixture was washed with 15 ml of DCM, 5 ml of water was added and phases were separated. Water phase was washed twice with DCM, all organic layers were combined, dried with phase separator filtration and evaporated to dryness to give 0.523 g of crude material. The product was purified by normal phase column chromatography (0-5% MeOH:DCM) to give 0.165 mg of the title compound. $^1$H-NMR (400 MHz; d6-DMSO; temp +300 K): Tautomer 1 (major 77%): δ 1.28 (t, 3H), 1.39 (d, 3H), 4.20-4.28 (m, 2H), (d, 1H), 4.75-4.85 (m, 1H) 5.43 (broad d, 1H), 6.54 (broad s, 1H), 13.28 (broad s, 1H). Tautomer 2 (minor 23%): δ 1.28 (t, 3H), 1.39 (d, 3H), 4.20-4.28 (m, 2H), 4.66-4.85 (m, 1H), 5.04-5.15 (broad s, 1H), 6.71 (broad s, 1H), 13.60 (broad s, 1H).

Example 10. Ethyl-5-((R)-1-hydroxyethyl)-1H-pyrazole-3-carboxylate

Zinc trifluoromethanesulfonate (1.037 g; 2.85 mmol) and (R)-(+)-3-butyn-2-ol (1.00 g; 14.27 mmol) were added to 2.98 ml (21.40 mmol) of $Et_3N$ under nitrogen atmosphere. Ethyldiazoacetate (1.80 ml; 21.40 mmol) was added slowly and then refluxed for 3 h. The mixture was cooled to RT and 45 ml of water was added. The mixture was extracted with 3×50 ml of DCM, organic layers were combined, dried with phase separator filtration and evaporated to dryness to give 2.503 g of crude material which was purified by normal phase column chromatography (0-10% MeOH:DCM) to give 0.671 mg of the title compound. $^1$H-NMR (400 MHz; d6-DMSO; temp +300 K): Tautomer 1 (major 78%): δ 1.28 (t, 3H), 1.39 (d, 3H), 4.18-4.35 (m, 2H), (d, 1H), 4.75-4.85 (m, 1H) 5.42 (broad d, 6.54 (s, 1H), 13.29 (broad s, 1H). Tautomer 2 (minor 22%): δ 1.28 (t, 3H), 1.39 (d, 3H), 4.18-4.35 (m, 2H), 4.66-4.85 (m, 1H), 5.09 (broad s, 1H), 6.71 (broad s, 1H), 13.61 (broad s, 1H).

Abbreviations

ACN: acetonitrile
DCM: dichloromethane
DIPEA: N,N-diisoprpyl-ethyl amine
DMF: dimethylformamide
DMSO: dimethylsulfoxide
EDCI×HCl: N-(3-dimethylaminopropyl)-N-ethylcarbodiimide hydrochloride
EtOAc: ethylacetate
EtOH: ethanol
HBTU: o-benzotriazole-N,N,N',N'-tetramethyl-uronium-hexafluoro-phosphate
KRED: ketoreductase (enzyme)
RT: room temperature
TFA: trifluoroacetic acid

The invention claimed is:

1. Crystalline form I' of N—((S)-1-(3-(3-chloro-4-cyanophenyl)-1H-pyrazol-1-yl)propan-2-yl)-5-((S)-1-hydroxyethyl)-1H-pyrazole-3-carboxamide (Ia) having an X-ray powder diffraction pattern comprising characteristic peaks at about 9.3, 15.7, 17.0, 24.1, and 25.1 degrees 2-theta, wherein the crystalline form I' is substantially free of any other crystalline form of N—((S)-1-(3-(3-chloro-4-cyanophenyl)-1H-pyrazol-1-yl)propan-2-yl)-5-((S)-1-hydroxyethyl)-1H-pyrazole-3-carboxamide (Ia).

2. Crystalline form I" of N—((S)-1-(3-(3-chloro-4-cyanophenyl)-1H-pyrazol-1-yl)propan-2-yl)-5-((R)-1-hydroxyethyl)-1H-pyrazole-3-carboxamide (Ib) having an X-ray powder diffraction pattern comprising characteristic peaks at about 9.2, 10.9, 15.1, 15.8, and 22.1 degrees 2-theta, wherein the crystalline form I" is substantially free of any other crystalline form of N—((S)-1-(3-(3-chloro-4-cyanophenyl)-1H-pyrazol-1-yl)propan-2-yl)-5-((R)-1-hydroxyethyl)-1H-pyrazole-3-carboxamide (Ib).

3. A process for preparing crystalline form I' or I" of N—((S)-1-(3-(3-chloro-4-cyanophenyl)-1H-pyrazol-1-yl)propan-2-yl)-5-((S)-1-hydroxyethyl)-1H-pyrazole-3-carboxamide (Ia) or N—((S)-1-(3-(3-chloro-4-cyanophenyl)-1H-pyrazol-1-yl)propan-2-yl)-5-((R)-1-hydroxyethyl)-1H-pyrazole-3-carboxamide (Ib), respectively, wherein the crystalline form I' or I" is substantially free of any other crystalline form of N—((S)-1-(3-(3-chloro-4-cyanophenyl)-1H-pyrazol-1-yl)propan-2-yl)-5-((S)-1-hydroxyethyl)-1H-pyrazole-3-carboxamide (Ia) or N—((S)-1-(3-(3-chloro-4-cyanophenyl)-1H-pyrazol-1-yl)propan-2-yl)-5-((R)-1-hydroxyethyl)-1H-pyrazole-3-carboxamide (Ib), respectively, comprising
  a) mixing N—((S)-1-(3-(3-chloro-4-cyanophenyl)-1H-pyrazol-1-yl)propan-2-yl)-5-((S)-1-hydroxyethyl)-1H-pyrazole-3-carboxamide (Ia) or N—((S)-1-(3-(3-chloro-4-cyanophenyl)-1H-pyrazol-1-yl)propan-2-yl)-5-((R)-1-hydroxyethyl)-1H-pyrazole-3-carboxamide (Ib) with a mixture of acetonitrile and water;
  b) heating the mixture from step a) to form a solution;
  c) cooling the solution from step b) to about 0-50° C.; and
  d) isolating the crystalline form.

4. The process according to claim 3, wherein the acetonitrile:water mixture has a volume ratio from about 85:15 to about 99:1.

5. The process according to claim 4, wherein the acetonitrile:water mixture has a volume ratio from about 90:10 to about 98:2.

6. The process according to claim 5, wherein the acetonitrile:water mixture has a volume ratio of about 95:5.

7. The process according to claim 3, wherein the cooling step c) occurs over about 5 to about 24 hours.

8. The process according to claim 7, wherein the cooling step c) occurs over about 6 to about 12 hours.

9. The process according to claim 3, wherein the isolated crystalline form is dried under vacuum at about 40° C. to about 60° C.

10. The crystalline form I' of N—((S)-1-(3-(3-chloro-4-cyanophenyl)-1H-pyrazol-1-yl)propan-2-yl)-5-((S)-1-hydroxyethyl)-1H-pyrazole-3-carboxamide (Ia) according to claim 1, further having an X-ray powder diffraction pattern comprising characteristic peaks at about 11.4, 14.9, 17.7, 20.5, and 27.2 degrees 2-theta.

11. The crystalline form I" of N—((S)-1-(3-(3-chloro-4-cyanophenyl)-1H-pyrazol-1-yl)propan-2-yl)-5-((R)-1-hydroxyethyl)-1H-pyrazole-3-carboxamide (Ib) according to claim 2, further having an X-ray powder diffraction pattern comprising characteristic peaks at about 7.9, 16.9, 18.4, 20.2, and 21.8 degrees 2-theta.

* * * * *